US006818779B2

(12) United States Patent  
Burk et al.

(10) Patent No.: US 6,818,779 B2  
(45) Date of Patent: Nov. 16, 2004

(54) THROMBOXANE LIGANDS WITHOUT BLOOD CLOTTING SIDE EFFECTS

(75) Inventors: Robert M. Burk, Laguna Beach, CA (US); Achim H-P Krauss, Foothill Ranch, CA (US); David F. Woodward, Lake Forest, CA (US)

(73) Assignee: Allergan, Inc., Irvine, CA (US)

( * ) Notice: Subject to any disclaimer, the term of this patent is extended or adjusted under 35 U.S.C. 154(b) by 17 days.

(21) Appl. No.: 10/213,190

(22) Filed: Aug. 5, 2002

(65) Prior Publication Data

US 2003/0109571 A1 Jun. 12, 2003

Related U.S. Application Data

(60) Continuation of application No. 09/899,713, filed on Jul. 5, 2001, now Pat. No. 6,462,077, which is a continuation-in-part of application No. 09/334,356, filed on Jun. 16, 1999, now abandoned, which is a continuation of application No. 09/038,068, filed on Mar. 11, 1998, now abandoned, which is a continuation of application No. 08/832,431, filed on Apr. 2, 1997, now Pat. No. 5,741,812, which is a continuation-in-part of application No. 08/645,467, filed on May 13, 1996, now Pat. No. 5,650,431, which is a continuation-in-part of application No. 08/378,414, filed on Jan. 26, 1995, now Pat. No. 5,516,791, which is a division of application No. 08/174,534, filed on Dec. 28, 1993, now Pat. No. 5,416,106.

(51) Int. Cl.$^7$ ................ C07D 307/00; C07D 311/00; C07D 321/02

(52) U.S. Cl. ................ 549/228; 549/397; 549/463; 568/820

(58) Field of Search .................. 549/228, 397, 549/463; 568/820

(56) References Cited

U.S. PATENT DOCUMENTS

| | | | |
|---|---|---|---|
| 4,436,934 A | 3/1984 | Larock | |
| 4,599,353 A | 7/1986 | Bito | |
| 4,622,339 A | 11/1986 | Lieb et al. | |
| 4,994,274 A | 2/1991 | Chan et al. | |
| 5,034,413 A | 7/1991 | Chan et al. | |
| 5,416,106 A | 5/1995 | Burk et al. | |
| 5,516,791 A | 5/1996 | Burk et al. | |

FOREIGN PATENT DOCUMENTS

EP 0 364417 4/1990

OTHER PUBLICATIONS

Starr. M.S., "Further Studies on the Effect of Prostaglandin on Intraocular Pressure in the Rabbit", *Exp. Eye Research*, 1971, 11, pp. 170–177.

Bito, L.Z., "Prostaglandins, Other Eicosanoids, and Their Derivatives as Potential Antiglaucoma Agents," *Applied Pharmacology in the Medical Treatment of Glaucomas* Drance, S.M. and Neufeld, A.H. eds., New York, Grune & Stratton, 1984, pp. 477–505.

Nilsson, et.al., "$PGF_{2\alpha}$ Increases Uveoscleral Outflow", *Invest. Ophthalmol. Vis. Sci.* (suppl), pp 284, 1987.

Siebold, et.al., "Esterified prostaglandin shows 'potent' promise", *Prodrug 5* pp. 3, 1989.

Bito, L.Z., "Prostaglandins, Old Concepts and New Perspectives", *Arch. Ophthalmol. 105*, pp. 1036, 1987.

Coleman, R.A., et al, "Comparison of the Actions of U–46619, A Prostaglandin $H_2$–Analogue, with Those of Prostagland $H_2$ and Thromboxane $A_2$ on some isolated Smooth Muscle Preparations", *Br. J. Pharmacol.* 73: pp. 773–778, 1981.

Burk et al; "A Safe and Efficient Method For Conversion of 1,2– and 1,3–Diols to Cyclic Carbonates Utilizing Triphosgene", *Tetrahedron Letters*, vol. 34, No. 3, pp. 395–398, 1993.

Primary Examiner—Fiona T. Powers  
(74) *Attorney, Agent, or Firm*—Robert J. Baran; Martin A. Voet; Carlos A. Fisher

(57) ABSTRACT

A method of treating ocular hypotension, hypertension, hemorrhage, myocardial ischemia, angina pectoris, coronary contraction, cerebrovascular contraction after subarachnoidal hemorrhage, cerebral hemorrhage and asthma which comprises administering to a mammal suffering therefrom a therapeutically effective amount of a thromboxane ligand which is a compound formula I,

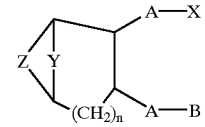

wherein Y is $(CH_2)_x$; Z is selected from the group consisting of

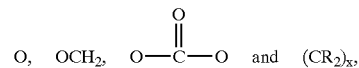

x is an integer of 1 or 2; n is 0 or 1; $R_2$ is hydrogen or an alkyl radical of from 1 to 4 carbons; A is an alkylene or alkenylene radical having from two to seven carbon atoms, which radical may be substituted with one or more hydroxy, oxo, alkyloxy or alkylcarboxy groups or said alkylene or alkenylene may have one or more enchained oxa or imino radicals; B is a methyl radical or a cycloalkyl radical having from three to seven carbon atoms, or an aryl radical, selected from the group consisting of hydrocarbyl aryl and heteroaryl radicals wherein the heteroatom is selected from the group consisting of nitrogen, oxygen and sulfur atoms, or substituted derivatives of said methyl, cycloalkyl or aryl radicals wherein said substituent is selected from the group consisting of halo, nitro, amino, thiol, hydroxy, alkyloxy and alkylcarboxy; and X is selected from the group consisting of nitro, cyano, —COOR, —$CH_2OR_1$, —$C(O)N(R_1)_2$, —$CH_2N(R_1)_2$—CH=N—OH and —$CH_2SR_1$ radicals wherein R is a $C_1$ to $C_{10}$ alkyl, phenyl or benzyl and $R_1$ is R or hydrogen; or a pharmaceutically acceptable salt thereof.

2 Claims, No Drawings

THROMBOXANE LIGANDS WITHOUT BLOOD CLOTTING SIDE EFFECTS

CROSS REFERENCE TO RELATED APPLICATIONS

This patent application is a continuation of U.S. patent application Ser. No. 09/899,713 filed on Jul. 5, 2001 now U.S. Pat. No. 6,462,077, which is a continuation in part of U.S. patent application Ser. No. 09/334,356 filed on Jun. 16, 1999, now abandoned, which is a continuation of U.S. patent application Ser. No. 09/038,068 filed on Mar. 11, 1998, now abandoned, which is a continuation of U.S. patent application Ser. No. 08/832,431 filed on Apr. 2, 1997, now U.S. Pat. No. 5,741,812, which is a continuation in part of U.S. patent application Ser. No. 08/645,467, filed on May 13, 1996, now U.S. Pat. No. 5,650,431, which is a continuation in part of U.S. patent application Ser. No. 08/378,414, filed on Jan. 26, 1995, now U.S. Pat. No. 5,516,791, which is a divisional of U.S. patent application Ser. No. 08/174,534, which was filed on Dec. 28, 1993, now U.S. Pat. No. 5,416,106.

BACKGROUND OF THE INVENTION

1. Field of the Invention

The present invention relates to thromboxane receptor ligands including a carboxylic acid group derivative, which do not cause blood clotting. In particular, the thromboxane receptor ligands are bicyclic carboxylic acid derivatives wherein said bicyclic rings may be hydrocarbyl or oxohydrocarbyl, e.g. 7-[carboxyalkyl or alkenyl]-6-[alkyl or alkenyl]-3-oxo-2,4-dioxobicyclo[3.2.1] octanes and derivatives thereof. In particular, hydroxyl, nitro, amino, amido, azido, oxime, thiol, ether and thiol ether derivatives of said carboxylic acid group are contemplated. In particular, 7-[6-carboxy-2-hexenyl]-6-[3-hydroxy-1-octenyl] 3-oxo-2,4-dioxobicyclo-[3.2.1] octane derivatives are disclosed. These compounds are useful as thromboxane agonists and antagonists. These compounds are also useful as ocular hypotensives.

2. Description of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Various U.S. Patents have recently issued which relate to thromboxane ligands and/or treating hemorrhaging. For example, U.S. Pat. Nos. 5,128,322; 5,128,354; 5,149,540; 5,389,630; 5,415,863; 5,436,260; 5,447,712; 5,482,960; 5,478,844 and 5,504,090 relate to methods of treating hemorrhaging. U.S. Pat. Nos. 5,248,507; 5,264,220; 5,382,569; 5,409,956; 5,443,848; 5,476,846; 5,480,645; 5,482,960 and 5,504,090 relate to thromboxane ligands. It is thus clear that a great deal of research is currently involved in thromboxane ligands, especially for treating hemorrhaging and related conditions.

SUMMARY OF THE INVENTION

We have found that certain bicyclic carboxylic acid derivatives, wherein said bicyclic rings may be hydrocarbyl or oxy hydrocarbyl, e.g. 7-[carboxylalkyl or alkenyl]-6-[alkyl or alkenyl]-3-oxo-2,4-dioxobicyclo[3.2.1] octane derivatives thereof, e.g. hydroxyl, nitro, amino, amido, azido, oxime, thiol, ether and thiol ether derivatives of said carboxy group are potent ocular hypotensive agents. We have further found that these compounds are thromboxane ligands and may have the unique ability, described herein, to mimic the vasoconstrictor properties of thromboxane A2 and its endoperoxide precursors, without causing concomitant platelet aggregation, i.e. blood clotting, and therefore said compounds provide a diverse variety of medical uses. Their potent vasoconstrictor properties may be safely used in therapy as they do not cause the platelet aggregation and resultant thrombosis that would arise from using known thromboxane mimetics.

The vasoconstrictor properties would substantially reduce blood flow in blood vessels and could be used to prevent hemorrhaging associated with external or internal injuries without the risk of thrombosis. These compounds may also be used as surgical adjuncts to reduce the bleeding from incisions at any anatomical location. Similarly, these compounds would be useful in limiting the bleeding associated with tooth extraction. The ability of these compounds to prevent hemorrhage, without causing platelet aggregation and resultant thrombosis, allows their safe application in systemic diseases where hemorrhage occurs. For example, bleeding from the gastro-intestinal tract associated with hemorrhoids, inflammatory bowel diseases, or gastric and peptic ulcer may be prevented. Bleeding associated with stroke may be prevented. Bleeding associated with stroke may be reduced without causing thrombosis and a potentially fatal complication. Bleeding is also a frequent complication in retinal diseases and surgeries resulting in impaired vision. This would also be amenable to safe treatment by the vascular-selective thromboxane mimetics described herein. Excessive bleeding associated with menstruation, childbirth, and uterine dysfunction may also be safely treated.

The selective vasoconstrictor properties of these compounds may be used to treat systemic hypotension. They may also be employed to restore normal blood pressure in haemorragic, anaphylactic, or septic shock episodes, without the serious risks associated with typical thromboxane mimetics which would result from their pro-aggregatory effects on platelets.

The selective vasoconstrictor properties may also be used to provide local anti-inflammatory effects in tissues such as the eye, skin, and nose. They may also be used to limit plasma exudation in burns and scalds.

A thromboxane-like vasoconstrictor that does not cause platelet aggregation may also be useful in optimizing blood born delivery of drugs and diagnostics in encapsulating vehicles. For example, delivery of drugs or diagnostic substances encapsulated in heat-sensitive or light-sensitive liposomes to the retina may be safely enhanced by agents described herein which selectively produce vasoconstriction.

Additionally, certain of the bicyclic carboxylic acid derivatives of the present invention are useful as thromboxane antagonists for treating systemic or pulmonary hypertension, myocardial ischemia, angina pectoris, coronary contraction, cerebrovascular contraction after subarachnoidal hemorrhage, cerebral hemorrhage and asthma.

Finally, the profound ocular hypotensive activity of these cyclic carbonate compounds is unexpected, given that the benchmark thromboxane/endoperoxide mimetic U-46619 (Coleman, R. A., et.al., Br. J. Pharmacol. 73:773–778, 1981) causes ocular hypertension in primates. The compounds herein would, therefore, be useful for treating glaucoma and ocular hypertension. They may be particularly useful as ocular surgical adjuncts for preventing ocular hypertensive episodes and reducing local bleeding that may occur post-surgically without complications inherent in blood clotting.

The present invention relates to methods of treating ocular hypertension and other diseases and conditions wherein thromboxane ligands are useful for treating which comprises administering an effective amount of a bicyclic carboxylic acid derivative represented by the formula I

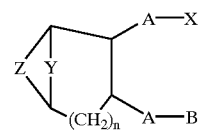

wherein Y is $(CH_2)_x$, Z is selected from the group consisting of

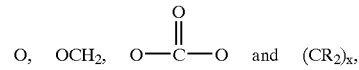

x is an integer of 1 or 2, n is 0 or 1; $R_2$ is hydrogen or an alkyl radical of from 1 to 4 carbons, e.g. methyl, or ethyl; A is an alkylene or alkenylene radical having from two to seven carbon atoms, e.g. about four to six carbon atoms, which radical may be substituted with one or more hydroxy, oxo, alkyloxy or alkylcarboxy groups or said alkylene or alkenylene may have one or more enchained oxa or imino radicals; B is a methyl radical or a cycloalkyl radical having from three to seven carbon atoms, e.g. about five to six carbon atoms, or an aryl radical, selected from the group consisting of hydrocarbyl aryl and heteroaryl radicals wherein the heteroatom is selected from the group consisting of nitrogen, oxygen and sulfur atoms; and X is selected from the group consisting of nitro, cyano, —COOR, —$CH_2OR_1$, —$C(O)N(R_1)_2$, —$CH_2N(R_1)_2$—CH=N—OH and —$CH_2SR_1$ radicals, wherein R is $C_1$ to $C_{10}$ alkyl, phenyl or benzyl and $R_1$ is R or hydrogen; or a pharmaceutically acceptable salt thereof. For example, A may be a straight chain alkylene radical, e.g. heptylene, or alkenylene radical, e.g. 3-hydroxy-1-heptylenyl, or an ethylenyloxyethylenyl radical or amino carbonyl hydrazino methyl radical and B may be selected from the group consisting of methyl, cyclopentyl, cyclohexyl, phenyl, thienyl, furanyl, pyridyl, etc. B may also be substituted by radicals selected from the group consisting of halo, e.g. fluoro, chloro, iodo etc., nitro, amino, thiol, hydroxy, alkyloxy, alkylcarboxy, etc. Preferably, B is methyl, cyclohexyl or phenyl.

DETAILED DESCRIPTION OF THE INVENTION

The present invention relates to the use of the compounds of formula I, above, as ocular hypotensives or a thromboxane ligands.

Preferably, the present invention relates to the use of a 7-[carboxylalkyl or alkenyl]-6-[alkyl or alkenyl]-3-oxo-2,4-dioxobicyclo[3.2.1] octane derivative, e.g. a hydroxyl, nitro, amino, amido, azido, oxime, thiol, ether or thiol ether derivative as thromboxane ligands. These preferred therapeutic agents are represented by compounds having the formula II,

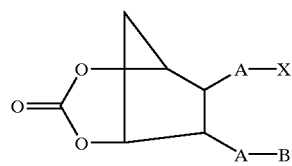

wherein A, B and X are as defined above.

For the purpose of this invention, unless further limited, the term "aliphatic" means linear and branched alkylene and alkenylene radicals, the terms "alkylene" and "alkenylene" mean divalent radicals derived from alkanes and alkenes, respectively. The term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about six, preferably one to about four carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

More preferably the method of the present invention comprises administering a 7-[carboxyalkyl or alkenyl]-6-[alkyl or alkenyl]-3-oxo-2,4-dioxobicyclo[3.2.1] octane derivative represented by the formula III,

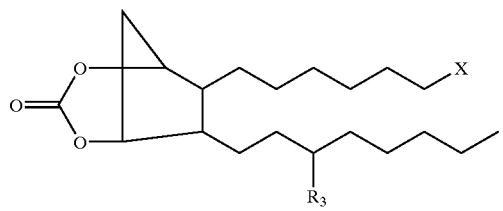

wherein either the α or ω chain may be unsaturated, i.e. the dashed bonds represent a single bond or a double bond which can be in the cis or trans configuration and $R_3$ is =O, —OH or —O(CO)$R_6$; wherein $R_6$ is a saturated or unsaturated acyclic hydrocarbon group having from 1 to about 20 carbon atoms, or —(CH$_2$)$_m$R$_7$ wherein m is 0–10, preferably 0–4; and $R_7$ is an aliphatic ring from about 3 to about 7 carbon atoms, or an aryl or heteroaryl ring, as defined above; or a pharmaceutically acceptable salt thereof.

Preferably the derivative used in the above method of treatment is a compound of formula IV,

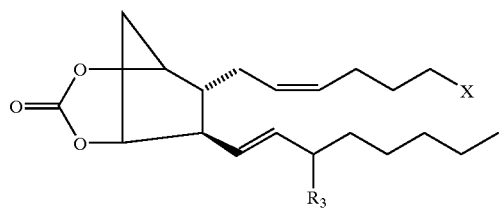

wherein hatched lines indicate the α configuration and a solid triangle is used to indicate the β configuration.

As an aromatic ring, $R_7$ preferably is phenyl, and the heteroaromatic rings have oxygen, nitrogen or sulfur as a heteroatom, i.e., $R_7$ may be thienyl, furanyl, pyridyl, etc.

In a further aspect, the present invention relates to pharmaceutical compositions comprising a therapeutically effective amount of a compound of formulae (I), (II), (III) or IV wherein the symbols have the above meanings, or a pharmaceutically acceptable salt thereof in admixture with a non-toxic, pharmaceutically acceptable carrier or liquid vehicle.

Preferred representatives of the compounds within the scope of the present invention are the compounds of formula IV wherein X are —COOR, —CH$_2$OH and —C(O)N(R$_1$)$_2$, wherein R and $R_1$ is defined above, and the pharmaceutically acceptable salts thereof. Specific compounds within the scope of this invention are as follows:

7-[6-carbomethoxy-2-cis-hexenyl-6-[3α-hydroxy-1-trans-octenyl]-3-oxo-2,4-dioxobicyclo[3.2.1]octane 7-[6-carbomethoxy-2-cis-hexenyl-6-[3α-pivaloyloxy-1-trans-octenyl]-3-oxo-2,4-dioxobicyclo[3.2.1]octane 7-[7-hydroxy-2-cis-heptenyl-6-[3α-hydroxy-1-trans-octenyl]-3-oxo-2,4-dioxobicyclo[3.2.1]octane 7-[6-carbobenzoxy-2-cis-hexenyl-6-[3α-hydroxy-1-trans-octenyl]-3-oxo-2,4-dioxobicyclo[3.2.1]octane 7-[6-carbobenzoxy-2-cis-hexenyl-6-[3α-pivaloyloxy-1-trans-octenyl]-3-oxo-2,4-dioxobicyclo[3.2.1]octane 7-[6-carboamino-2-cis-hexenyl-6-[3α-hydroxy-1-trans-octenyl]-3-oxo-2,4-dioxobicyclo[3.2.1]octane 7-[6-carboisopropylamino-2-cis-hexenyl]-6-[3α-hydroxy-1-trans-octenyl]-3-oxo-2,4-dioxobicyclo[3.2.1]octane 7-[6-carboxy-2-cis-hexenyl-6-[3α-pivaloloxy-1-trans-octenyl]-3-oxo-2,4-dioxobicyclo [3.2.1]octane

[1R-[1α, 4α, 5β(Z), 6α(1E, 3S*)-7-[6-(3-hydroxy-1-octenyl)-2-oxabicyclo[2.2.1]hept-5-yl]-5-hepten-1-ol

[1S-[1α, 2β(Z), 3(1E, 3R*), 5α]]-7-[3-(3-hydroxy-1-octenyl)-6,6-dimethybicyclo[3.1.1]hept-2-yl]-5-hepten-1-ol

[1S-[1α, 2α(Z), 3β (1E, 3S*), 4α]]-7-[3-(3-hydroxy-4-(4-iodophenoxy)-1-butenyl]-7-oxabicyclo[2.2.1]hept-2-yl]-5-hepten-1-ol

[1S-[1α, 2α(5Z), 3α, 4α]]-7-[3-[2-(phenylamino)-carbonyl]hydrazino]methyl]-7-oxabicyclo[2.2.1]hept-2-yl]-5-hepten-1-ol A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, amines, etc.

The compounds utilized in the method of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of formulas I through IV or a corresponding pharmaceutically acceptable salt of a compound of formulas 1 through IV.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active compounds is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit: doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use, the compounds utilized in the method of this invention are administered at the initial dosage of about 0.01 mg to about 10 mg/kg daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Pharmaceutical compositions for treating glaucoma or lowering intraocular pressure may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, (sodium EDTA) although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compound of the present invention depends on the specific compound, and on the condition to be treated; the selection of the appropriate dose is well within the knowledge of the skilled artisan.

The ophthalmic formulation so the present invention are conveniently packaged in forms suitable for metered application, such as in containers equipped with a dropper, to facilitate application to the eye. Containers suitable for dropwise generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 $\mu$l.

This invention is further illustrated by the following non-limiting examples

EXAMPLE 1

CUCLOPENTANE HEPTENOIC ACID, 5-CIS-2-(3α-T-BUTYLDIMETHYL-SILYLOXY-1-TRANS-OCTENYL)-3,5-DIHYDROXY, [1α, 2β, 3α, 5α] METHYL ESTER

PGF2α(542 mg, 1.53 mmol) was dissolved in ethylether (Et$_2$O) (20 mL) and cooled to 0° C. A solution of CH$_2$N$_2$ in Et$_2$O was added dropwise to the above suspension until a yellow color persisted. The solution was warmed to 25° C. for 0.5 h and then concentrated in vacuo to yield PGF 2α methyl ester as an oil.

The crude ester was heated at reflux with n-butyl boronic acid (0.188 g, 1.84 mmol) in CH$_2$Cl$_2$(3.1 mL) for 2 h. The volatiles were removed under vacuum to yield the crude boronate ester which was immediately diluted with CH$_2$Cl$_2$ (3 mL) and cooled to 0° C. 2,6-Lutidine (0.43 mL, 3.7 mmol) was added followed by t-butyldimethylsilyl trifluoromethane-sulfonate (0.67 mL, 2.9 mmol). The reaction solution was then warmed to 23° C. for 16 h, concentrated, and rediluted with methanol (40 mL). After stirring for 24 h, the methanol was removed under vacuum and the residue was purified by FCC (2:1 hexane (hex)/ethyl acetate (EtOAc), silica gel) to yield (0.697, 92% yield) of the named product as an oil.

EXAMPLE 2

7-[6-CARBOMETHOXY-2-CIS-HEXENYL]-6-[3α-T-BUTYLDIMETHYLSILYLOXY-1-TRANS-OCTENYL]-3-OXO-2,4-DIOXOBICYCLO [3.2.1] OCTANE 149 mg (0.318 mmol) of the compound of Example 1 were dissolved in 1.6 ml of CH$_2$Cl$_2$ and cooled to at −78° C.

0.154 mL (0.6 mmol) of pyridine were then added and stirring was continued for 5 minutes. 48 mg (0.5 mmol) of triphosgene dissolved in 1 mL CH$_2$Cl$_2$ was slowly added and the resulting mixture was stirred for an additional hour before being allowed to slowly warm to room temperature. After standing overnight the reaction was quenched with saturated aqueous NH$_4$Cl, diluted with EtOAc and the resulting reaction mixture was worked up washing the organic portion with 1 N HCl, NaHCO$_3$ and brine. The organic layer was dried over anhydrous MgSO$_4$, filtered and concentrated in vacuo to yield 149 mg of a crude fraction including the named compound.

EXAMPLE 3

7-[7-HYDROXY-2-CIS-HEPTENYL]-6-[3α-T-BUTYLDIMETHYLSILYLOXY-1-TRANS-OCTENYL]-3-OXO-2,4-DIOXOBICYCLO [3.2.1] OCTANE 73 mg (0.143 mmol) of the compound of Example 2 were dissolved in a 0.28 mL of ethylether (Et$_2$O) and then 3.0 mg of lithium borohydride (LiBH$_4$) were added and the mixture stirred at 23° C. overnight. The reaction was quenched using 2.0 N NaOH and the resulting reaction mixture was worked up by extraction with EtOAc and washing the organic portion with brine. The resulting organic layer was concentrated in vacuo and dried over anhydrous MgSO$_4$ to yield 63 mg of the named compound.

EXAMPLE 4

7-[7-HYDROXY-2-CIS-HEPTENYL]-6-[3α-HYDROXY-1-TRANS-OCTENYL]-3-OXO-2,4-DIOXOBICYCLO [3.2.1] OCTANE 14 mg (0.03 mmol) of the compound of Example 3 were dissolved in THF and 0.045 mL of a 1.0 M solution of tetrabutyl ammonium fluoride (Bu$_4$NF) were added. After stirring under argon at room temperature for 5 hours the resulting reaction mixture was worked up by dilution with EtOAc and washing with H$_2$O. The organic layer was dried over anhydrous MgSO$_4$, filtered, and concentrated in vacuo to yield 83 mg of crude product. The crude product was purified by elution on silica gel with a solution of 60% EtOAc in hexane to yield the named compound.

EXAMPLE 4a

CYCLOPENTANE HEPTENOIC ACID, 5-CIS-2-(3-T-BUTYLDIMETHYLSILYLOXY-1-TRANS-OCTENYL)-3,5-DIHYDROXY,[1α, 2β, 3α, 5α] BENZYL ESTER

A solution of the ester of Example 1 (556 mg, 1.17 mmol) in 0.5 N aqueous lithium hydroxide (3.5 mL, 1.76 mmol) and THF (7.0 mL) was stirred at 23° C. for 24 h and acidified with 10% citric acid. The mixture was extracted with EtOAc and the combined organics were dried (MgSO$_4$), filtered and concentrated in vacuo.

The crude residue was treated with O-benzyl-N,N'-diisopropylisourea (0.41 g, 1.76 mmol) and heated to 65° C. in benzene (7.0 mL) for 24 h. The reaction was cooled to room temperature and stripped of the solvent. Flash column chromatography (silica gel, 2:1 hexane/EtOAc) of the residue gave 553 mg (85%) of the named compound.

EXAMPLE 5

7-[6-CARBOBENZOXY-2-CIS-HEXENYL]-6-[3α-T-BUTYLDIMETHYLSILYLOXY-1-TRANS-OCTENYL]-3-OXO-2,4-DIOXOBICYCLO [3.2.1] OCTANE 330 mg (0.591 mmol) of the compound of Example 4a were treated in accordance with the procedure of Example 2 to yield 235.7 mg (68% yield) of the named compound.

EXAMPLE 6

7-[6-CARBOBENZOXY-2-CIS-HEXENYL]-6-[3α-HYDROXY-1-TRANS-OCTENYL]-3-OXO-2,4-DIOXOBICYCLO [3.2.1] OCTANE 60 mg (0.1037 mmol) of the compound of Example 5 in 1.0 mL of THF was treated with 0.20 mL a 1.0 M solution of $Bu_4NF$ and stirred at 23° C. for 16 hours. The reaction mixture was diluted with EtOAc, and then washed, consecutively, with $H_2O$ and brine and dried over anhydrous $MgSO_4$. The dried organic phase was filtered and the filtrate concentrated under vacuum. Elution on silica gel with a 1:1 mixture of hexane and EtOAc yielded 29.7 mg (62% yield) of the named compound.

EXAMPLE 7

7-[6-CARBOXY-2-CIS-HEXENYL]-6-[3α-HYDROXY-1-TRANS-OCTENYL]-3-OXO-2,4-DIOXOBICYCLO [3.2.1] OCTANE

A suspension of 25 mg (0.0531 mmol) of the compound of Example 6 and 8 mg of a catalyst comprising 10% Palladium, by weight, on carbon in a 1:4 mixture 1-methyl-1,4-cyclohexadiene and methanol (1.25 mL) was heated at 35° C. In 20 minutes the reaction was complete and the reaction mixture was diluted with $CH_2Cl_2$ and filtered. The filtrate was concentrated in vacuo and eluted on silica gel with EtOAc to yield 20 mg (99% yield) of the named compound.

EXAMPLE 8

CYCLOPENTANE HEPTENOIC ACID, 5-CIS-2-(3α-HYDROXY-1-TRANS-OCTENYL)-3,5-HYDROXY, [1α, 2β, 3α, 5α] BENZYL ESTER 1.75 g (4.93 mmol) of the prostaglandin $F_{2α}$ were mixed with 1.73 g (7.40 mmol) of O-benzyl-N,N'-diisopropylisourea in 25 mL of benzene and heated to 65° C. for 4 h. After removal of the solvent, treatment by consecutive elution on silica gel with a 1:1 mixture of hexane and EtOAc followed by 95:5 mixture of EtOAc and methanol gave 2.08 g (95% yield) of the named compound.

EXAMPLE 9

CYCLOPENTANE HEPTENOIC ACID, 5-CIS-2-(3α-PIVALOYLOXY-1-TRANS-OCTENYL)-3,5-DIHYDROXY, [1α, 2β, 3α, 5α] BENZYL ESTER 1.13 gm (2.54 mmol) of the compound of Example 8 and 0.39 g (3.81 mmol) of n-butylboronic acid in 28 mL of toluene were heated at reflux for 72 hours with azeotropical removal of water. The reaction mixture was cooled to 23° C. and concentrated in vacuo. The residue was diluted with $CH_2Cl_2$ and allowed to react with 0.77 mL (3.81 mmol) of trimethylacetylchloride, 1.06 mL (7.63 mmol) of triethylamine and 155 mg (1.27 mmol) of DMAP (4-dimethylaminopyridine) at 23° C. for 48 hours. The resulting reaction mixture was concentrated, in vacuo, dissolved in methanol and stirred overnight. The methanol was removed in vacuo and the residue was purified by elution on silica gel with a 2:1 mixture of hexane and EtOAc to afford 0.87 gm (65% yield) of the named compound was obtained.

EXAMPLE 10

CYCLOPENTANE HEPTENOIC ACID, 5-CIS-2-(3α-PIVALOYLOXY-1-TRANS-OCTENYL)-3-HYDROXY, 5-IMIDAZOLYLOXY [1α, 2β, 3α, 5α] BENZYL ESTER 211 mg (0.399 mmol) of the compound of Example 9 and 77.7 mg (0.479 mmol) of 1,1-carbonyldiimidazole were dissolved in 1.0 mL of $CH_2Cl_2$ and stirred for 24 hours at 23° C. to yield the named compound.

EXAMPLE 11

7-[6-CARBOBENZOXY-2-CIS-HEXENYL]-6-[3α-PIVALOYLOXY-1-TRANS-OCTENYL]-3-OXO-2,4-DIOXOBICYCLO[3.2.1]OCTANE 0.133 mmol of the compound of Example 10 and 0.14 mL (1.33 mmol) of t-butylamine dissolved in $CH_2Cl_2$ were heated to 45° C. for 48 hours. The reaction mixture was cooled to room temperature, concentrated in vacuo and eluted on silica gel with a 3:1 mixture of hexane and EtOAc to yield 31 mg (42% yield) of the named compound.

EXAMPLE 12

7-[6-CARBOXY-2-CIS-HEXENYL]-6-[3α-PIVALOYLOXY-1-TRANS-OCTENYL]-3-OXO-2,4-DIOXOBICYCLO[3.2.1] OCTANE

The compound of Example 11 was treated according to the procedure of Example 7 to yield the named compound.

EXAMPLE 13

CYCLOPENTANE HEPTENAMIDE, 5-CIS-2-[3α-T-BUTYLDIMETHYLSILYLOXY-1-TRANS-OCTENYL)-3,5 DIHYDROXY, [1α, 2β, 3α, 5α]

460 mg (0.954 mmol) of the compound of Example 1 was reacted with an excess of $NH_3$ in 6.0 mL of methanol to yield a solution including the named compound. The excess solvent and unreacted $NH_3$ were evaporated and the residue was purified by elution on silica gel, consecutively, with 100% EtOAc followed by a 9:1 mixture of $CH_2Cl_2$ and methanol to yield 395 mg (89% yield) of the named compound.

EXAMPLE 14

7-[6-CARBOAMINO-2-CIS-HEXENYL]-6-[3α-T-BUTYLDIMETHYLSILYLOXY-1-TRANS-OCTENYL]-3-OXO-2,4-DIOXOBICYCLO[3.2.1] OCTANE 256 mg (0.548 mmol) of the compound of Example 13, 5 mg (0.040 mmol) of 4-dimethylamino pyridine (DMAP) and 98 mg. (0.602 mmol) of 1,1 carbonyldiimidazole were reacted in 1.5 ml of $CH_2Cl_2$, for 24 hours at 23° C. The resulting reaction solution was concentrated in vacuo and the residue purified by elution with 100% EtOAc. The resulting reaction product was stirred with 71 uL DBU (0.474 mmol) in 1.0 mL of benzene for 24 hours at 23° C. After concentration in vacuo and elution on silica gel with a 2:1 mixture of EtOAc and hexane, 25 mg (10% yield) of the named compound were obtained.

EXAMPLE 15

7-[6-CARBOAMINO-2-CIS-HEXENYL]-6-[3α-HYDROXY-1-TRANS-OCTENYL]-3-OXO-2,4-DIOXOBICYCLO[3.2.1] OCTANE

The compound of Example 14 was converted into the named compound at 95% yield by the procedure of Example 6.

EXAMPLE 16

7-[6-CARBOXY-2-CIS-HEXENYL]-6-[3α-T-BUTYLDIMETHYLSILYLOXY-1-TRANS-OCTENYL]-3-OXO-2,4-DIOXOBICYCLO[3.2.1] OCTANE 156 mg (0.267 mmol) of the compound of Example 5 were treated in accordance with the procedure as Example 7 to yield the corresponding carboxylic acid (99%) yield).

EXAMPLE 17

7-[6-CARBOISOPROPYLAMINO-2-CIS-HEXENYL]-6-[3α-HYDROXY-1-TRANS-OCTENYL]-3-OXO-2,4-DIOXOBICYCLO [3.2.1] OCTANE 75 mg (0.151 mmol) of the compound of Example 16 in $CH_2Cl_2$ were reacted with 1.5 mL of $SOCl_2$ at 0° C. for 1 h. 69 mg (1.17 mmol) of isopropylamine were added and the resultant solution was warmed to 23° C. for 16 h to yield a reaction mixture which upon removal of the excess solvent and purification by elution on silica gel with a 1:1 mixture of hexane and EtOAc gave 4.8 mg (8% yield) of the named compound.

EXAMPLE 18A

CYCLOPENTANE HEPTENOIC ACID, 5-CIS-2-(3α-PIVALOYLOXY-1-TRANS-OCTENYL)-3,5-DIHYDROXY, [1α, 2β, 3α, 5α] METHYL ESTER $PGF_2α$ methyl ester (prepared as described in Example 1) was treated according to the procedure of Example 9 to yield the named compound.

EXAMPLE 18B

CYCLOPENTANE HEPTENOIC ACID, 5-CIS-2-(3α-PIVALOYOLOXY-1-TRANS-OCTENYL)-3-HYDROXY, 5-IMIDAZOLYOXY, [1α, 2β, 3α, 5α] METHYL ESTER

A solution of the compound of Example 18A (75 mg 0.166 mmol) in THF (1.0 mL) was heated to 50° C. and triphosgene (16.4 mg, 0.0553 mmol) was added. After 2 h imidazole (22.6 mg, 0.332 mmol) was added and a white precipitate formed immediately. The reaction was stirred an additional 16 h, allowed to cool to room temperature, and concentrated in vacuo. Purification of the residue by FCC (1:1 hex/EtoAc, silica gel) afforded the 45.3 mg of the named compound, i.e 50% yield.

EXAMPLE 18C

7-[6-CARBOMETHOXY-2-CIS-HEXENYL]-6-[3α-PIVALOYLOXY-1-TRANS-OCTENYL]-3-OXO-2,4-DIOXOBICYLO [3.2.1]OCTANE

A solution of the compound of Example 18B (17.4 mg, 0.032 mmol) in benzene (0.75 mL) was treated with 1,8-diazabicyclo [5.4.0] undec-7-ene (DBU) (24 μL, 0.159 mmol) at 23° C. After 12 h the reaction solution was concentrated in vacuo and the residue was purified by FCC (1:1 hex/EtoAc, silica gel) to give 12.9 mg (85% yield) of the named compound.

EXAMPLE 19

[1R-[1α, 4α, 5β(Z), 6α(1E, 3S*)-7-[6-(3-hydroxy-1-octenyl)-2-oxabicyclo[2.2.1]hept-5-yl]-5-hepten-1-ol A solution of U-46619 (10 mg, 0.0285 mmol) in methyl acetate (1.0 mL) was treated with diazomethane in ether (~½ mL) at 0°. The resultant yellow solution was allowed to warm to room temperature, concentrated in vacuo to give 10.3 mg (99%) of the methyl ester of U-46619.

Lithium borohydride (28 ul of a 2.0 M solution in tetrahydrofuran THF, 0.0565 mmol) was added to a solution of the methyl ester of U-46619 (10.3 mg, 0.282 mmol) in diethylether ($Et_2O$)(1.5 mL) at 23° C. After 24 h TLC indicated only a lower Rf product. The reaction was quenched with IN NaOH, stirred 1 h and extracted with $CH_2Cl_2$. The organic portion was dried over $Na_2SO_4$, filtered and concentrated in vacuo. Flash column chromatography (silica gel, 1:1 hexane/EtOAc) gave 9.0 mg (95%) of alcohol.

EXAMPLE 20

[1S-[1α, 2β(Z), 3(1E, 3R*), 5α]]-7-[3-(3-hydroxy-1-octenyl)-6,6-dimethylbicyclo[3.1.1]hept-2-yl]-5-hepten-1-ol The title compound was prepared in accordance with the procedures described above in Example 19 with Pinane thromboxane $A_2$ replacing U-46619.

EXAMPLE 21

[1S-[1α, 2α(Z), 3β(1E, 3S*), 4α]]-7-[3-(3-hydroxy-4-(4-iodophenoxy)-1-butenyl]-7-oxabicyclo[2.2.1] hept-2-yl]-5-hepten-1-ol The title compound was prepared in accordance with the procedures described above in Example 19 with I-BOP replacing U-46619.

EXAMPLE 22

[1S-[1α, 2α(5Z), 3α, 4α]]-7-[3-[2(phenylamino) carbonyl]-hydrazino]methyl]-7-oxabicyclo [2.2.1] hept-2-yl]-5-hepten-1-ol The title compound was prepared in accordance with the procedures described above in Example 19 with SQ-29,548 replacing U-46619.

PROSTANOID RECEPTOR ACTIVITY

Activity at different prostanoid receptors was measured in vitro in isolated smooth muscle preparations. FP-activity was measured as contraction of the isolated feline iris sphincter. $EP_1$-activity was measured as contraction of the longitudinal smooth muscle of the isolated guinea pig ileum. $EP_3$-activity was measured as inhibition of the twitch response induced by electrical field stimulation in the isolated guinea pig was deferens and as contraction of the longitudinal smooth muscle of the isolated chick ileum. TP-vasoconstrictor activity was measured as contraction of rings of the isolated rat thoracic aorta. Effects on platelets from healthy human donors were measured by incubating platelet-rich plasma with the compounds described herein. Inhibition of aggregation was determined by the ability of the compounds described herein to inhibit platelet aggregation in platelet-rich plasma induced by 20 µM ADP. The activity profile of various compounds is reported in Tables 1 and 7.

In addition, inhibition by the thromboxane A2-receptor antagonist SQ29,548 ([1S-[1α, 2α (5Z), 3α, 4α]]-7-[3-[[2-[phenylamino)carbonyl]-hydrazino]methyl]-7-oxabicyclo [2.2.1] hept-2-yl]-5-heptenoic acid) of vasoconstrictor activity was investigated. For that purpose, activity of the compound of Example 4, the compound of Example 7, and U-46619 (9,11-dideoxy-9α,11α-methanoepoxy prostaglandin $F_{2α}$), a potent and stable thromboxane $A_2$ analog, was measured in rings of the isolated rat thoracic aorta, first in the absence and then in the presence of SQ29,548 (1 uM). The results are reported in Table 2.

EXAMPLE 23

Pharmacological Selectivity for a TP-Receptor Subtype Present on Vascular Smooth Muscle Examination of Tables 1 and 7 reveals an unexpected and unique trend in biological activity associated with certain examples of formula IV. Typically, thromboxane (TP-) receptor agonists indiscriminately cause both platelet aggregation and smooth muscle contraction. It has, therefore, been concluded that there is no convincing evidence that subtypes of the TP-receptor exist (Jones, R. L., Wilson, N. H., Armstrong, R. A., Tymkewycz, P. M. Colloque INSERM 152:335–344, 1987). Examples 4, 15 and 16 and 19 through 21 exhibit pronounced activity in contracting vascular smooth muscle but have no or minimal ability to cause platelet aggregation.

Further evidence is provided below to demonstrate that the ability of examples 4, 15 and 16 and 19 through 21 to cause contraction of vascular smooth without causing platelet aggregation involves selective stimulation of a subtype of TP-receptor present on vascular smooth muscle.

1. A TP-receptor antagonist blocks the effect of agonists which are selective for the vascular TP-receptor (Example 4) and non-selective with respect to vascular and platelet TP-receptors (Example 7, U-46619), see Table 2. This shows that Example 4 and its congeners, which show selectivity for contracting vascular smooth muscle, produce their effect by interacting with a subtype of TP-receptor as opposed to some other type of eicosanoid receptor.

2. The compound Example 4 neither causes platelet aggregation nor inhibits the ability of U-46619 or Example 7 to cause platelet aggregation, see Table 3. Moreover, Example 4 did not inhibit ADP or arachidonic acid induced platelet aggregation (Table 4) and, therefore, its activity cannot be ascribed to a mechanism which opposes the aggregatory response, e.g., behaving as a prostacyclin or prostaglandin D2 mimetic, inhibition of cyclooxygenase.

Thus, it appears that certain examples of formula IV selectively constrict smooth muscle by stimulating a TP-receptor subtype which exists on smooth muscle but not on platelets. Such antagonists may be useful in treating systemic and local vasoconstriction and other indications without concommitant inhibition of normal platelet function and blood clotting.

EXAMPLE 24

Effects on Intraocular Pressure

The effects of four examples of formula TV and the thromboxane mimetic U-46619 on intraocular pressure are provided in the following tables. The compounds were prepared at the said concentrations in a vehicle comprising 0.1% polysorbate 80 and 10 mM TRIS base. Dogs and monkeys were treated by administering 25 ul to the ocular surface, the contralateral eye received vehicle as a control. Intraocular pressure was measured by applanation pneumatonometry. Experiments were performed with dogs and monkeys. Dog intraocular pressure was measured immediately before drug administration and at 2, 4 and 6 hour thereafter. Additional studies in monkeys were performed over a 5 day period and drug was administered at times 0, 6, 24, 30, 48, 54, 72, 78, and 96 hours. Monkey intraocular pressure was recorded just before drug administration on each day and at the 2 and 4 hour time intervals between dosing.

The examples of formula IV examined showed a pronounced ocular hypotensive effect in both dogs and monkeys (Tables 5 and 6). In contrast, the thromboxane/endoperoxide mimetic U-46619 produced an increase in intraocular pressure. Thus, the cyclic carbonate derivatives described herein caused a profound decrease in intraocular pressure which was unexpected given the absence of ocular hypotensive activity associated with U-46619. Since the in vitro pharmacological effects of the cyclic carbonate analogs (a) cannot be attributed to stimulation of other known prostanoid receptors and (b) are susceptible to a thromboxane antagonist, it is concluded that the ocular hypotensive activity of these compounds is related to selective stimulation of a thromboxane receptor subtype.

The foregoing description details specific methods and compositions that can be employed to practice the present invention, and represents the best mode contemplated. However, it is apparent from one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. In particular, other thromboxane ligands comprising a carboxylic acid derivative may be prepared from the parent carboxylic acid to obtain thromboxane receptor agonists which are useful in treating hemorrhage by constricting the cardiovascular network without the side effect of causing blood clotting or thromboxane antagonists, which are useful in treating hypertension without the side effect of causing blood clotting. Thus, in general TRL-COOH, wherein TRL represents a thromboxane receptor ligand residue may be converted by methods known in the art to TRL-W, wherein W is $C(O)(NR_1)_2$, $CH_2OR_1$, $CH_2N(R_1)_2$ or COOR wherein R and $R_1$ are as defined above. Certain compounds which are useful as TRL-COOH are described in CRC Handbook of Eicosanoids: Prostaglandins and Related Lipids Vol. I: Part B, at pages 35–40 and Developments in the Characterization of Prostaglandin Endoperoxide/Thromboxane Receptors, Colloque INSERM, Vol. 152, 1987, pp 335 to 344 which references also refer in many instances to methods for preparing such compounds. These compounds are described in Tables 8 and 9 below. In addition, the compounds represented by formulae: I and II may have the following orientation:

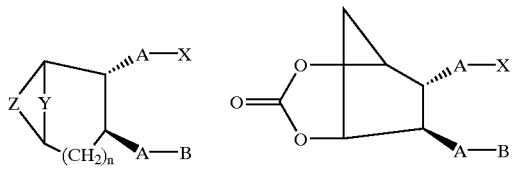

Thus, however detailed the foregoing may appear in text, it should not be construed as limiting the overall scope hereof, rather, the ambit of the present invention is to be governed only by the lawful construction of the appended claims.

TABLE 4

Effect of Example 4 on Agonist-Induced Platelet Aggregation Induced by Arachidonic Acid and ADP

| Agonist: | Agonist Response: % of max response | 10-7 M Example 4 pretreatment | 10-6 M Example 4 pretreatment |
|---|---|---|---|
| 800 µM Arachidonic Acid | 101.6 + 1.3 | 98.0 + 1.8 | 98.8 + 1.1 |
| 20 µM ADP | 100 + 0 (standard) | 99.9 + 1.4 | 97.6 + 1.8 |
| 2 µM ADP | 73.8 + 11.17 | 68.3 + 12.9 | 73.1 + 14.3 |

TABLE 3

Effect of Example 4 on Example 7 and U46619-induced Platelet Aggregation

| Agonist: | Agonist Response: % of max response | 10-7 M Example 4 pretreatment | 10-6 M Example 4 pretreatment |
|---|---|---|---|
| 10-9 Example 7 | 0 | | |
| 10-8 Example 7 | -7.9 + 1.3 | -8.4 + 0.9 | -8.0 + 2.9 |
| 3.3 × 10-8 Example 7 | -8.8 + 1.3 | -9.0 + 1.6 | -7.3 + 0.7 |
| 10-7 Example 7 | 100.5 + 2.2 | 97.8 + 1.7 | 99.5 + 1.7 |
| 10-6 Example 7 | 103.0 + 1.9 | 95.3 + 0.9 | 96.5 + 0.9 |
| 10-8 U46619 | 0 | | |
| 10-7 U46619 | -7.0 + 1.1 | -5.5 + 1.1 | -5.6 + 0.9 |
| 3.3 × 10-7 U46619 | 97.7 + 1.6 | 93.8 + 2.3 | 94.2 + 2.8 |
| 10-6 U46619 | 100.0 + 1.9 | 94.6 + 2.6 | 96.0 + 0.8 |

TABLE 5

The effect of compounds of Formula IV and U-46619 (9,11-dideoxy-9α,11α, methanoepoxy prostaglandin $F_{2\alpha}$) on dog intraocular pressure.

| FORMULA III | (Dose %) | INTRAOCULAR PRESSURE CHANGES AT PREDETERMINED TIMES (hr) AFTER DOSING | | |
|---|---|---|---|---|
| | | 2 HR | 4 HR | 6 HR |
| U-46619 | 0.1% | +0.86 | +1.75 | +2.7 |
| Example 7 | 0.01% | -9.7** | -11.4** | -11.25** |
| Example 4 | 0.1% | -6.7** | -7.7** | -8.5** |

TABLE 1

EFFECT OF EXAMPLES OF FORMULA IV AT DIFFERENT PROSTANOID RECEPTOR SUBTYPES
COMPOUND $EC_{50}$ (nM) VALUES AT PROSTANOID RECEPTOR SUBTYPES

| | FP (Cat Iris) | $EP_1$ (Guinea Pig Ileum) | $EP_3$(c) Guinea Pig vas deferens) | $EP_3$(d) (Chick Ileum) | $TP_{VASC}$ (Rat Aorta) | Platelets (Human) Aggregation | Inhibition of Aggregation |
|---|---|---|---|---|---|---|---|
| Example 7 | 433 | 1,240 | 282 | 245 | 0.23 | 24 | N/A |
| Example 4 | 485 | N/A | 2,930 | >$10^4$ | 1.0 | >$10^4$ | N/A |
| Example 17 | 3,020 | | | | 324 | N/A | N/A |
| Example 15 | 387 | | | | 58 | 3,110 | N/A |

$EC_{50}$ (nM) = nM concentration required to produce a 50% of maximal response

TABLE 2

EFFECT OF THE THROMBOXANE (TP)-RECEPTOR ANTAGONIST SQ 29548 ON CONTRACTION OF THE RAT AORTA PRODUCED BY EXAMPLES OF FORMULA IV

| COMPOUND | $EC_{50}$ at $TP_{VASC}$-RECEPTOR | |
|---|---|---|
| | SQ29.548 | +SQ29.548 |
| Example 7 | 2 | 325 |
| Example 4 | 0.9 | 454 |
| U-46619 | 1.3 | 8,080 |

| | | | | |
|---|---|---|---|---|
| Example 11 | 0.1% | −6.9** | −7.7** | −9.4** |
| Example 12 | 0.1% | −3.8** | −4.7** | −6.9** |

**p < 0.01, Student's paired t test

TABLE 6

The effect of compounds of Formula IV and U-46619
(9,11-dideoxy-9α,11α, methanoepoxy prostaglandin $F_{2α}$)
on monkey intraocular pressure.

INTRAOCULAR PRESSURE CHANGES AT PREDETERMINED TIMES (HR) AFTER DOSING.

| Formula III | Dose (%) | 0 | 2 | 4 | 6 | 24 | 26 | 28 | 30 | 48 |
|---|---|---|---|---|---|---|---|---|---|---|
| U-46619 | | 0 | 2.0** | 0.3 | 1.0* | | | | | |
| Example 7 | 0.01% | 0 | −0.4 | 0 | 0 | −1.0 | 3.2 | −4.6* | −3.2** | −1.8 |

INTRAOCULAR PRESSURE CHANGES AT PREDETERMINED TIMES (HR) AFTER DOSING.

| | 50 | 52 | 54 | 72 | 74 | 76 | 78 | 96 | 98 | 100 |
|---|---|---|---|---|---|---|---|---|---|---|
| U-46619 | | | | | | | | | | |
| Example 7 | −3.8 | −4.0* | −4.2* | 4.2* | −2.0 | −3.2 | −4.0 | −2.0 | −2.2 | −3.2* |

*p < 0.05 Students' paired t test
**p < 0.01

TABLE 7

| Compound | $EC_{50}$ (nM) (Rat Aorta) aggreg | Platelets inhib | |
|---|---|---|---|
| U-46619 | 10 | 320 nM | NA |
| Example 19 | 26 | NA | NA |
| Pinane Thrombozone $A_2$ | 203 | 950 | |

TABLE 7-continued
| | EC$_{50}$ (nM) (Rat Aorta) aggreg | Platelets inhib | |
|---|---|---|---|
| 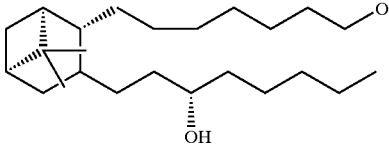 Example 20 | 929 | NA | |
| 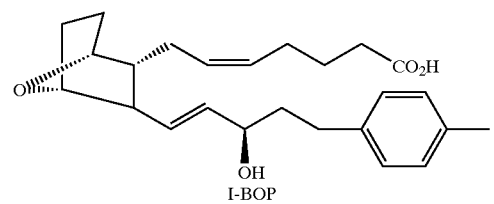 I-BOP | 2.0 | 214 nM | NA |
| 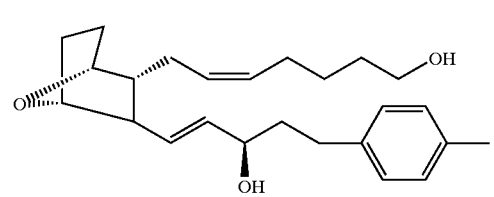 Example 21 | 0.4 | NA | NA |
| 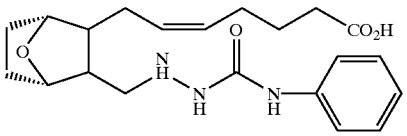 SQ-29-543 | K$_B$ = 1.6 | K$_B$ = 30.6 nM | |
| 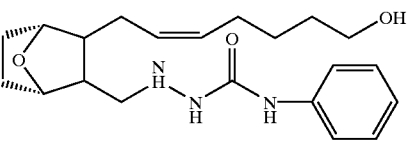 Example 22 | K$_B$ = 18.2 | K$_B$ = 4500 nM | |

TABLE 8

TXA ANALOGS

| No. | Systematic name | Structure | Mol. formula (mol. wt.) | Synthesis | Biological actions |
|---|---|---|---|---|---|
| 1 | 9α,11α-Carba-15a-hydroxythromba-(Z15,(E)13-dienoic acid | 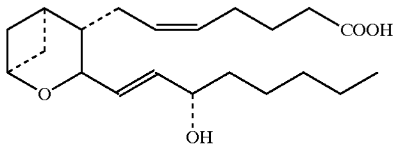 | $C_{27}H_{54}O_4(350)$ | From 1-(3-hydroxy-trans-1-propenyl)cyclobutan-3-one[1] | Inhibitor of $PGH_2$-induced aggregation of HPRP[1] |
| 2 | 9α,11α-Epoxy-15α-hydroxy-11a-carbathromba-(Z15,(E)13-dienoic acid | 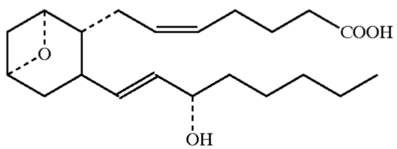 | $C_{21}H_{14}O_4(350)$ | Via a Demjanov-Tiffenau[2] ring expansion of $PGA_2$ methyl ester 15-t-butyldimethysilyl ether to a 6-membered enone which was conjugated, epoxidized, reduced to a 9,11-diol and cyclized to the oxetane[3] | Contracted rat aortic strip: $CD_{10}$ $10^{-1}$ Ar[2] |
| 3 | Methyl 9α,11α-epithia-15α-hydroxy-thromba(Z)5,(E)13-dienoate | 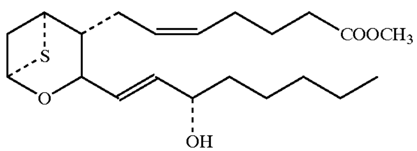 | $C_{21}H_{14}O_4S(382)$ | From $TXB_2$ methyl ester 11-methyl ether 15-benzoate by inversion of 11a-OH, mesylation, formation of 11-methoxycarbonylethylthio derivative, and cyclization[4] | |
| 4 | 9α,11α-Carba-15α-hydroxy-11α-carbathromba-(Z)5,(E)13-dienoic acid (carbocyclic $TXA_2$) | 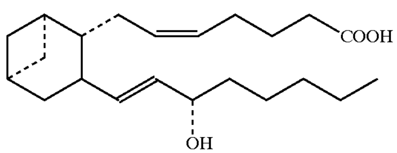 | $C_{22}H_{16}O_3(348)$ | From 2-formylbicyclo[3.1.1]hept-2-ene;[1] for other syntheses see Refs. 6, 7 | Potent $TXA_2$-like agonist on the vasulature but profound TXA antagonist on the aggregation of platelets; profound constriction of isolated perfused coronary arteries (e.g., cat; $10^1 \times TXB_2$) Exacerbated ischemic damage in the heart (without induction of platelet aggregation) during coronary insufficiency (anesthetized cat. i.v.) |
| 7 | 2,3,4-Trinor-1,5-inter-m-phenylene-9α,11α-dimethylcarba-15a-hydroxy-11α-carbathromba-(E)5,(E)13-dienoic acid | 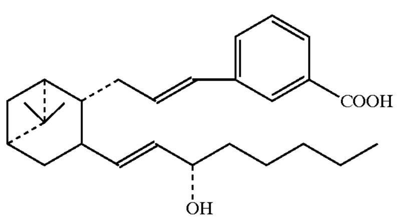 | $C_{21}H_{14}O_4(410)$ | From (−) myrtenol[11] | Inhibited vasoconstriction of isolated perfused cat coronary artery induced by carbocyclic $TXA_2$ by 72% at 1 μM[11] |

TABLE 8-continued

TXA ANALOGS

| No. | Systematic name | Structure | Mol. formula (mol. wt.) | Synthesis | Biological actions |
|---|---|---|---|---|---|
| 8 | 9α,11α-Dimethylcarba-15α-hydroxy-16-(4-fluorophenoxy)-ω-tetranor-11α-carbathromba-(Z)5,(E)13-dienoic acid | 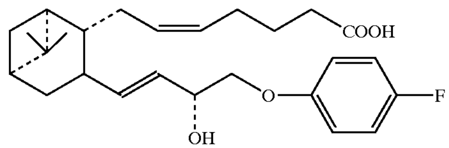 | C$_{26}$H$_{23}$FO$_4$(430) | From nopol[12] | Precipitated irreversible aggregation of HPRP at 0.31 μM[12], partial agonist in the rabbit aorta, dog saphenous vein, and guinea pig trachea assays[11] |
| 9 | 9α,11α-Dimethylcarba-13-aza-13H-15α- and 15β-hydroxy-20-n-propyl-11α-carbothromba-(Z)5,(E)13-enoic acid | 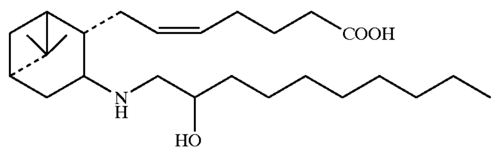 | C$_{26}$H$_{14}$NO$_3$(421) | | TXA$_2$ antagonist on platelets and vasculature; inhibited aggregation of HPRP induced by STA$_2$ (compound 10), 9,11-methanoepoxy PGH$_2$, AA, collegen, and ADP (second phase but not first) with IC$_{50}$ values of 0.11–0.38 μM; also inhibited TXA$_2$ induced aggregation of HPRP but had no effect on cycloxygenase, TX synthetase, or PGE$_2$ synthetase I.V. infusion in guinea pigs or cats (1–10 μg/kg/min) caused ex vivo inhibition of AA or STA$_2$-induced aggregation Inhibited vasoconstricior response in vitro (rat aorta) and in vivo (guinea pig, i.v.) induced by stable endoperoxide and TXA$_2$ analogs[11] |
| 10 | 9α,11α-Epithia-15α-hydroxy-11α-carbathromba-(Z)5,(E)13-dienoic acid (STA$_2$) | 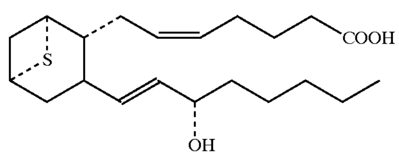 | C$_{21}$H$_{14}$O$_3$S (366) | From trans-1-formyl-2-methoxycarbonylcyclohex-4-ene,[11] also from PGA$_2$ methyl ester 15-acetate[14] | Potent, full TXA$_2$ agonist on platelets and vasculature Caused rapid irreversible aggregation of HPRP; IC$_{50}$ = .06 μM Constricted isolated rat aorta, CD$_{50}$ = 0.4 nM, and was a vasoconstrictor in vivo (i.v., guinea pig)[11] |
| 11 | Methyl 9α,11α-carba-15α-hydroxy-11α-thiathromba-(Z)5,(E)13-dienoate | 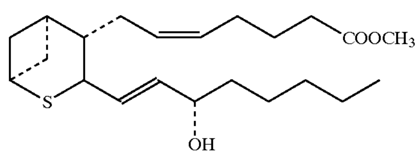 | C$_{21}$H$_{16}$O$_3$S (380) | From 3-vinylcyclobutanone[15] | Contracted isolated rat aorta; CD$_{50}$ = 5 × 20$^{-1}$ g/mf; no effect on HPRP[11] |

TABLE 8-continued

TXA ANALOGS

| No. | Systematic name | Structure | Mol. formula (mol. wt.) | Synthesis | Biological actions |
|---|---|---|---|---|---|
| 12 | 9α,11α-Carba-15α-hydroxy-11α-iminothromba-(Z)5, (E)13-dienoic acid | 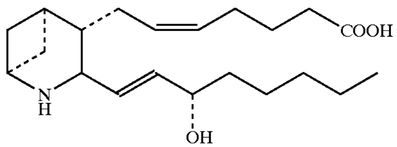 | $C_{21}H_{16}NO_3$ (349) | From cis-3-formylcyclobutanol[11] | Contracted isolated rat aorta; $CD_{50} = 3 \times 10^{-1}$ g/mf; no effect on HPRP[11] |
| 13 | 9α,11α-Epithia-15α-hydroxy-11α-thiathromba-(Z)5,(E)13-dienoic acid | 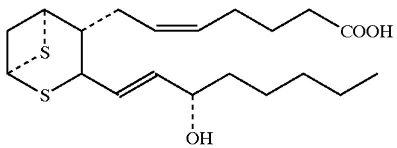 | $C_{20}H_{33}O_3S_2$ (384) | From 4,4-dimethoxy-2-(6-chloro-2-hexyn-1-yl)-acetoacetate[11] | Contracted isolated rat aorta; $CD_{50} = 7 \times 10^{-10}$ M; irreversible aggregation of HPRP; $IC_{50} = 4.3 \times 10^{-6}$ M[11] |
| 14 | 9α-11-Methanoepoxy-15α- and 15β-hydroxythromba (Z)5,(E)13-dienoic acid | 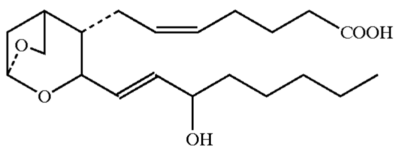 | $C_{21}H_{34}O_3$ (366) | From the product of methylenation of trans-cis-cis-N,N-dimethyl-2-benzyloxy-6-methoxytetrahydropyran-4-one-3-acetamide which was obtained from the Corey lactone[22,31] | Weak $TXA_2$ agonist; contraction of rabbit aortic strips; 0.04 × $TXA_2$; aggregation of rabbit PRP; 0.001 × $TXA_2$; did not antagonize aggregatory effect of $TXA_2$ nor was $TXA_2$ synthetase inhibited[11] |
| 15 | 9α-Methanoepoxy-10-oxa-11α-carba-15α- and 15β-hydroxythromba-5-cis-13-trans-dienoic acid | 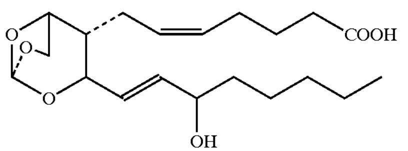 | $C_{21}H_{16}O_3$ (366) | From trans-cis-cis-N,N-dimethyl-2,4-bis-hydroxymethyl-6-methoxytetrahydropyran-3-acetamide[11] | Contraction of rat aortic strips; 0.02 × $TXA_2$; did not aggregate rabbit PRP, antagonize the aggregatory effect of $TXA_2$, or inhibit $TXA_2$ synthetase[11] |
| 16 | 9α,11α-Epoxy-10α-homo-15α- and 15β-hydroxy-11α-carbathromba-(Z)5,(E)13-dienoic acid | 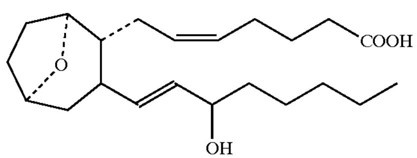 | $C_{22}H_{34}O_4$ (364) | From [4 + 3] adduct of furan and tetrabromoacetone[10] | No effect on blood platelets; weak vasoconstrictor activity[10] |
| 17 | | 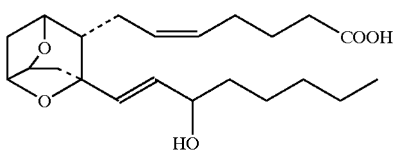 | $C_{22}H_{34}O_3$ (378) | From 1-dimethoxymethyl-2-styryl-8-oxabicyclo [3,2,1] oct-6-en-3-ol[24] | Mixture of C-15 epimers has strong $TXA_2$-like activity[14] |

TABLE 9
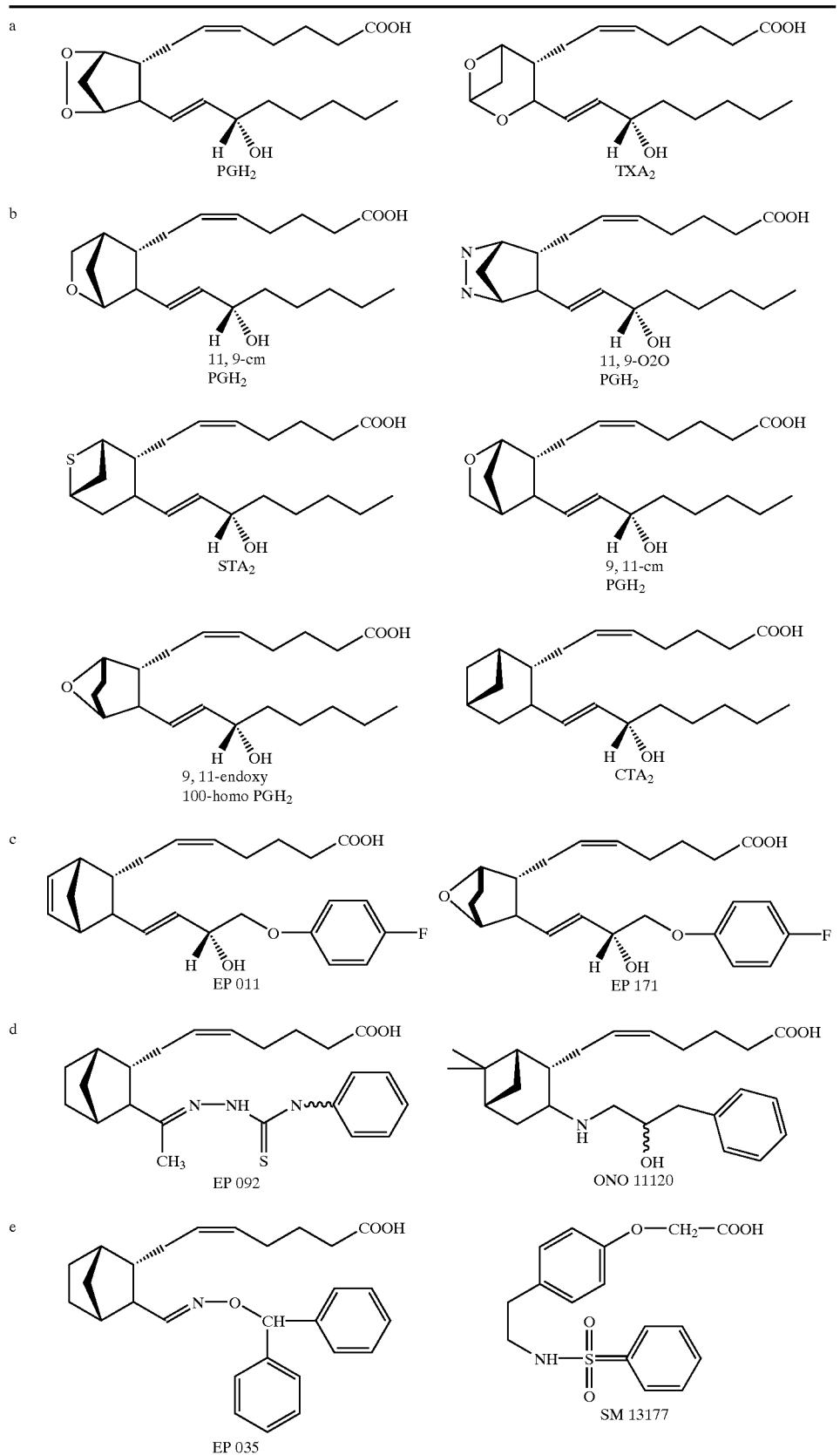

TABLE 9-continued

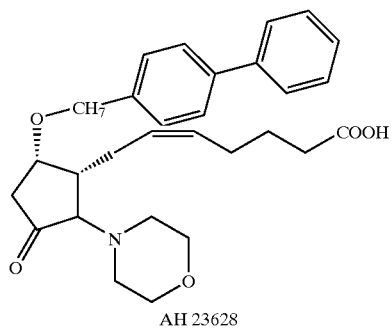

AH 23628

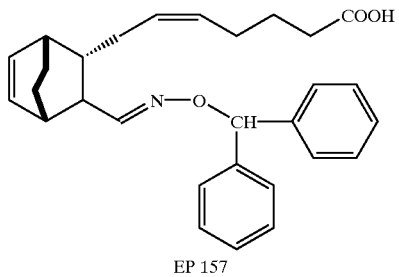

EP 157

Structures of (a) the natural compounds PGH$_2$ and TXA$_2$. (b) stable thromboxane mimetics with natural side chains. (c) potent 16-p-fluorophenoxy prostanoics (d) specific thromboxane receptor antagonists and (e) thromboxane receptor antagonists with prostacyclin-like activity.

What is claimed is:

1. A method for preparing a thromboxane agonist or antagonist having reduced ability to cause platelet aggregation, i.e. blood clotting, which comprises converting a thromboxane ligand having the formula TRL-COOH, wherein TRL represents a thromboxane receptor ligand residue to TRL-W wherein is selected from the group consisting of CH$_2$OR$_1$, wherein R$_1$ is hydrogen.

2. The method of claim 1 wherein said thromboxane agonist is [1S-[1α, 2α(Z), 3β (1E, 3S*), 4α]]-7-[3-(3-hydroxy-4-(4-iodophenoxy)-1-butenyl]-7-oxabicyclo[2.2.1]hept-2-yl]-5-hepten-1-ol.

* * * * *